United States Patent [19]
Wong

[11] Patent Number: 5,650,624
[45] Date of Patent: Jul. 22, 1997

[54] PASSIVE INFRARED ANALYSIS GAS SENSOR

[75] Inventor: Jacob Y. Wong, Goleta, Calif.

[73] Assignee: Engelhard Sensor Technologies, Inc., Goleta, Calif.

[21] Appl. No.: 422,507

[22] Filed: Apr. 13, 1995

[51] Int. Cl.$^6$ .................................................. G01N 21/61
[52] U.S. Cl. ................................ 250/338.5; 250/339.04; 250/339.13
[58] Field of Search ................ 250/339.04, 338.5, 250/339.13, 343

[56] References Cited

U.S. PATENT DOCUMENTS

| | | | |
|---|---|---|---|
| 3,032,655 | 5/1962 | Romans | 250/338.5 |
| 3,662,171 | 5/1972 | Brengman et al. | 250/339.04 |
| 3,793,525 | 2/1974 | Burch et al. | 250/343 |
| 3,811,776 | 5/1974 | Blau, Jr. | 356/51 |
| 4,500,207 | 2/1985 | Maiden | 356/409 |
| 4,520,265 | 5/1985 | Griggs et al. | 250/338.5 |
| 4,527,896 | 7/1985 | Irani et al. | 356/43 |
| 4,578,762 | 3/1986 | Wong | 364/497 |
| 4,694,173 | 9/1987 | Wong | 250/343 |
| 4,709,150 | 11/1987 | Burough et al. | 250/338 |
| 4,722,612 | 2/1988 | Junkert et al. | 374/124 |
| 4,765,752 | 8/1988 | Beynon et al. | 374/127 |
| 4,790,324 | 12/1988 | O'Hara et al. | 128/664 |
| 4,980,847 | 12/1990 | Hirano | 364/557 |
| 5,026,992 | 6/1991 | Wong | 250/343 |
| 5,041,723 | 8/1991 | Ishida et al. | 250/339.13 |
| 5,060,508 | 10/1991 | Wong | 73/31.02 |
| 5,163,332 | 11/1992 | Wong | 73/863.23 |
| 5,165,796 | 11/1992 | Gat et al. | 250/339.04 |
| 5,186,541 | 2/1993 | Paulk | 374/124 |
| 5,222,389 | 6/1993 | Wong | 73/31.02 |
| 5,326,173 | 7/1994 | Evans et al. | 374/128 |
| 5,340,986 | 8/1994 | Wong | 250/343 |

OTHER PUBLICATIONS

Acton et al., "Remote Measurement of Carbon Monoxide by a Gas Filter Correlation Instrument", AIAA Journal 11 (7), Jul. 1973, pp. 899–900.

U.S. patent application Serial No. 08/284,914, filed Aug. 2, 1994 by J. Wong.

Brochure dated Jun. 16, 1993 regarding OAI MIR–100 Thermopile (2 pgs.).

Thermopile MIR–100 Line Catalog Book (6 pgs.) (Apr. 1993).

ARMTEC Industries, Inc. brochure regarding Northwoods PS–20 detector (2 pgs.) (undated).

*Primary Examiner*—Carolyn E. Fields
*Attorney, Agent, or Firm*—Lyon & Lyon LLP

[57] ABSTRACT

A passive source infrared gas detector which uses an ambient temperature source and the space between the detector assembly and the source as the sample chamber is provided, the gas detector includes an infrared detector assembly for producing a first output, a second output, and a third output, the first output being indicative of the radiation received by the detector assembly at a first non-neutral spectral band which is absorbable by a preselected gas to be detected, the second output being indicative of the radiation received by the detector assembly at a first neutral spectral band from the passive infrared source, and the third output being indicative of the radiation received by the detector assembly at a second neutral spectral band from the passive infrared source. Signal processing means are included for manipulating the three outputs to determine the concentration of the gas being monitored. By adding additional detectors to the detector assembly which can detect radiation at spectral bands characteristic of additional gases, the infrared gas detector can be used to monitor the concentration of a plurality of gases.

20 Claims, 6 Drawing Sheets

| PASSIVE SOURCE TEMP °C/°K | R3.91μ ×10⁻⁴ Wcm⁻²μ⁻¹ | R4.67μ ×10⁻⁴ Wcm⁻²μ⁻¹ | R5.00μ ×10⁻⁴ Wcm⁻²μ⁻¹ | R3.91/R5.00 | R5.00/R3.91 |
|---|---|---|---|---|---|
| 5 / 278 | 0.7304 | 2.5907 | 3.8267 | 0.1909 | 5.2392 |
| 10 / 283 | 0.9229 | 3.1511 | 4.5946 | 0.2009 | 4.9784 |
| 15 / 288 | 1.1566 | 3.8067 | 5.4818 | 0.2110 | 4.7396 |
| 20 / 293 | 1.4384 | 4.5691 | 6.5009 | 0.2213 | 4.5195 |
| 22 / 295 | 1.5663 | 4.9067 | 6.9485 | 0.2254 | 4.4365 |
| 25 / 298 | 1.7758 | 5.4507 | 7.6655 | 0.2317 | 4.3166 |
| 30 / 303 | 2.1772 | 6.4647 | 8.9898 | 0.2422 | 4.1291 |
| 35 / 308 | 2.6517 | 7.6250 | 10.488 | 0.2528 | 3.9552 |
| 40 / 313 | 3.2092 | 8.9462 | 12.177 | 0.2636 | 3.7944 |
| 45 / 318 | 3.8608 | 10.444 | 14.071 | 0.2744 | 3.6446 |

*FIG. 3*

PASSIVE INFRARED ANALYSIS GAS SENSOR

BACKGROUND OF THE INVENTION

1. Field of the Invention

The present invention generally relates to the field of gas sensing devices. More particularly, the present invention relates to gas detectors capable of measuring the concentrations of one or more gases using a characteristic infrared absorption band of the gas to be detected.

2. Description of the Prior Art

Many gases have characteristic absorption bands falling within the infrared spectrum. The nondispersive infrared (NDIR) technique has been widely used in the gas analyzer industry for the detection of these gases. Such gas analyzers utilize the principle that various gases exhibit substantial absorption at characteristic wavelengths in the infrared radiation spectrum. Typically, a narrow-band optical or infrared transmission filter is used to isolate the wavelength band of interest in NDIR gas analyzers. On the other hand, a prism or diffraction grating is used in gas analyzers relying on dispersive techniques.

The NDIR technique, which is generally classified as a non-interactive gas analysis technique, offers a number of advantages over previous interactive types of gas measurement methods including electrochemical fuel cell, sintered semiconductor (tin dioxide), catalytic (platinum bead) and thermal conductivity. These advantages include speed of response, gas detection specificity, long term measurement stability, reduced maintenance, and greater specificity. Moreover, in some cases the interactive gas sensor can be poisoned into a nonfunctional state. Depending on the application, this could place human life at risk.

Interactive gas sensors are generally nonspecific because the reagent being used to determine the concentration of the desired gas may react with other gases that are present. This will naturally result in false readings. Further, if the equilibrium of the reaction between the nonspecific gas and the reagent is such that the gas and reagent remain reacted even after the partial pressure of the gas drops in the environment being monitored, the sensor will no longer function properly and is poisoned.

The response time for NDIR gas sensors is typically shorter than that for interactive gas sensors because the kinetics of the reaction between the sample gas and reagent controls how quickly the reactive type sensor can detect a change in the concentration of the gas in the environment being monitored.

Despite the fact that interactive gas sensors are unreliable and that the NDIR gas measurement technique is one of the best, NDIR gas analyzers have not enjoyed wide spread application because of their complexity and high cost of implementation.

Over the years, a large number of measurement techniques based upon the NDIR principle for the detection of gases have been proposed and successfully demonstrated. In the past, NDIR gas analyzers typically included an infrared source, a motor-driven mechanical chopper to modulate the source, a pump to push or pull gas through a sample chamber, a narrow bandpass interference filter, a sensitive infrared detector plus expensive infrared optics and windows to focus the infrared energy from the source onto the detector.

The most notable of these types of analyzers are shown and described in U.S. Pat. No. 3,793,525 to Burch, et al., U.S. Pat. No. 3,811,776 to Blau, Jr., and U.S. Pat. No. 4,578,762 to Wong. These NDIR gas analyzers perform well functionally and have contributed greatly to the overall technical advancement in the field of gas analysis during the past two decades. However, their overall size, complexity, and cost have precluded their use in a number of applications.

The need for better and lower cost gas analyzers has led to newer inventions. For example, U.S. Pat. No. 4,500,207 to Maiden and U.S. Pat. Nos. 4,694,173 and 5,026,992 to Wong have proposed NDIR techniques for gas detection that do not use any moving parts such as mechanical choppers. The goal of these patents has been to produce NDIR gas sensors that are more rugged and compact, thus opening up a host of new applications.

In an attempt to further reduce the cost and simplify the implementation of the NDIR technique, a low-cost NDIR gas sensor technique was developed. The low-cost NDIR technique employs a diffusion-type gas sample chamber of the type disclosed in U.S. Pat. No. 5,163,332, issued in Nov. 17, 1992, to the present applicant, and hereby incorporated by reference. This diffusion-type gas sample chamber eliminates the need for: expensive optics, mechanical choppers, and a pump for pushing or pulling the gas into the sample chamber. As a result, a number of applications for the NDIR technique, which were previously considered impractical because of cost and complexity, have been opened.

A similar guiding principle led to the development of the improved NDIR gas sensor disclosed by Wong in U.S. Pat. No. 5,444,249. This patent describes a simple, low-cost diffusion-type NDIR gas sensor which can be micromachined out of a semiconductor material such as Si or GaAs, thus allowing the entire sensor to be placed on a microchip.

Although the low-cost NDIR gas sensor technique of U.S. Pat. No. 5,163,332 and the improved NDIR gas sensor of U.S. Pat. No. 5,444,249 have opened a wide variety of new applications, these gas sensors still require too much power to be used in many potential gas sensor applications. As a result, applications in which low-cost, solid-state gas sensors may be used remain limited.

If a gas analysis technique could be developed which required no moving parts, had the same degree of specificity as the NDIR technique, was low cost, and had relatively low power demands so that devices employing the technique could be battery operated over an extended period of time, the applications in which gas sensors are used and the frequency of their use would increase dramatically. Therefore, while a long felt need exists for a simple, compact, inexpensive gas sensor that has low power requirements, this need has gone unfilled. Accordingly, a goal of the present invention is to further advance the technique of infrared gas analysis by providing a compact, reliable, low cost, and low power infrared gas sensor using infrared absorption.

SUMMARY OF THE INVENTION

The present invention is directed toward an infrared gas sensor for detecting the concentration of one or more predetermined gases using a novel infrared gas analysis technique referred to as passive infrared analysis (PIA). The PIA technique of the present invention is simpler than the NDIR gas analysis techniques known to date in that it does not require an "active" infrared source, nor does it require a structurally defined sample chamber. As a result, small, solid-state, low-cost and low power gas sensors can be constructed to meet a host of special applications hitherto impossible using presently available NDIR gas analyzers.

The present invention recognizes that all objects greater than 0 kelvin emit radiation. The present invention takes advantage of this fact by using ordinary objects, such as walls, ceilings, floors, etc. as a "passive" source of infrared radiation. These "passive" infrared radiation sources can be effectively used to replace the "active" infrared radiation sources that have been used almost exclusively hitherto in all NDIR gas analyzers.

The "active" infrared source used in conventional NDIR gas sensors is typically a heated and very hot object (500°–1000° C.) such as nichrome wire imbedded in alumina ceramic (Nerst glower) or a resistive tungsten wire of a small incandescent light bulb. These sources are characterized as "active" sources because they are powered by the gas sensor. On the other hand, a "passive" source, as used herein, is any object that is above 0 kelvin, but which is not powered by the gas detector power supply. Typical passive infrared sources that will be used by the infrared gas sensor of the present invention include walls, carpets, tile floors, ceilings, and furnace walls to name just a few. Clearly, however, as those skilled in the art will recognize from the teachings of the present disclosure, the passive infrared sources which can be used by the gas sensor of the present invention are virtually unlimited.

Although the temperature of active infrared sources is very high, the source area is typically quite small. A source area on the order of a few $mm^2$ is not uncommon. On the other hand, although the temperature of typical indoor passive infrared source is only about 300 K or ~25° C., if the utilized source area is approximately 1000 times larger than that of conventional infrared sources, then using Planck's equation it can be shown that the spectral radiant emittance for the passive infrared source is comparable to that of conventional active sources in the spectral region from 3 to 20 microns. The passive infrared source area required for proper gas detection will depend on the temperature range expected from the source.

In the PIA technique employed in the present invention, the passive infrared source must be characterized. To characterize the passive infrared source at least two infrared detectors are used to measure the spectral emittance from the selected passive infrared source at two "neutral" spectral bands. These spectral bands are chosen so that they are not absorbed by any of the gases to be found in the environment to be measured. Based on Plank's Law, the ratio of outputs measured at the two neutral spectral bands can be used to uniquely determine the temperature of the passive infrared source assuming the two neutral spectral bands are close enough so that the variation of the emissivity function for the source is insignificant.

To determine the concentration of the gas to be detected, the detector assembly also measures the amount of incident radiation at a "non-neutral" spectral band that coincides with an absorption band of the gas to be measured. This output, therefore, is indicative of the concentration of the gas within the angle subtended by the detector assembly to the passive infrared source. By using the output measured at at least one of the neutral spectral bands, the output measured at the non-neutral spectral band and the calculated temperature, the concentration of the gas within the angle subtended by the detector assembly to the passive infrared source can be determined.

According to one embodiment of the present invention, a passive source infrared gas detector which uses an ambient temperature source and the space between the detector assembly and the source as the sample chamber is provided, the gas detector comprises an infrared detector assembly for producing a first output, a second output, and a third output, the first output being indicative of the radiation received by the detector assembly at a first non-neutral spectral band which is absorbable by a preselected gas to be detected, the second output being indicative of the radiation received by the detector assembly at a first neutral spectral band from the passive infrared source, and the third output being indicative of the radiation received by the detector assembly at a second neutral spectral band from the passive infrared source. Signal processing means are included for manipulating the three outputs to determine the concentration of the gas being monitored. By adding additional detectors to the detector assembly that can detect radiation at spectral bands characteristic of additional gases, the infrared gas detector can be used to monitor the concentration of a plurality of gases.

According to another embodiment of the present invention, a passive source infrared gas detector is provided which comprises:

a. an infrared detector assembly comprising
  i. a port for receiving radiation therethrough from the passive infrared source,
  ii. a first sensor, a second sensor, and a third sensor disposed to receive radiation through the port for producing a first output, a second output, and a third output indicative of the radiation incident on the first sensor, second sensor, and third sensor, respectively,
  iii. a first narrow band pass filter interposed between the port and the first sensor, the first narrow band bass filter producing an output therefrom indicative of the radiation incident on the first band pass filter at a first non-neutral spectral band which is absorbable by a preselected gas to be detected,
  iv. a second narrow band pass filter interposed between the port and the second sensor, the second narrow band pass filter producing an output therefrom indicative of the radiation incident on the second band pass filter at a first neutral spectral band, and
  v. a third narrow band pass filter interposed between the port and the third sensor, the third narrow band pass filter producing an output therefrom indicative of the radiation incident on the third band pass filter at a second neutral spectral band,
b. temperature measuring means for producing an output corresponding to the ambient temperature of the first, second, and third sensors;
c. signal processing means adapted to receive the outputs from the first sensor, second sensor, third sensor, and temperature measuring means and for sampling and at least temporarily storing the outputs of the first sensor, second sensor, third sensor, and temperature measuring means at preset intervals, the signal processing means including means for
  i. correcting the stored outputs of the first sensor, second sensor, and third sensor to compensate for the ambient temperature of the first sensor, second sensor, and third sensor, respectively, for the sampling period,
  ii. calculating the temperature of the passive infrared source for the sampling period based on the ratio of the corrected values of the outputs from the second and third sensors,
  iii. calculating a predicted output for at least one of the second or third sensors based on the calculated temperature of the passive infrared source for the sampling period, iv. calculating an attenuation factor by comparing the predicted output of at least one of the second or third sensors with the corrected output from the corresponding sensor for the sampling period, v. correcting the stored output of the first sensor by the attenuation factor, vi. determining the concentration of the gas for the sampling period from the corrected output from the first sensor, and vii. monitoring the concentration of gas based on a predetermined function and providing an output signal based on the monitoring.

Thus, the infrared gas sensor according to the present invention uses a passive infrared source in a novel PIA technique which effectively eliminates the need for a hot "active" infrared source that is used in conventional NDIR gas measurement devices. Furthermore, in the PIA technique employed in the infrared gas sensor of the present invention, the space between the passive infrared source, for example a certain portion of a wall, and the detector assembly becomes the sample chamber. In other words, the present invention not only eliminates the "active" infrared source, but it also eliminates the need for the sample chamber used in conventional NDIR gas analyzers.

Due to the fact that an "active" infrared source is not required for the implementation of the present invention, the power consumption of a infrared gas sensor according to the present invention can be significantly reduced, thus making the simple passive infrared gas sensor of the present invention battery operable for an extended period of time. Moreover, the size of the sensor can be reduced because a structurally defined gas chamber is no longer necessary.

Accordingly, it is an object of this invention to provide an apparatus and method for measuring the concentration of one or more gases using a novel infrared analysis technique referred to as passive infrared analysis (PIA).

Further objects and advantages of the invention will be better understood from the following description considered in connection with accompanying drawings in which the preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 3 is a table depicting the value of the ratio of the spectral radiant emittances for wavelengths 5.00 and 3.91 microns as a function of the temperature of the "passive" infrared source. The emissivity values for both spectral bands are assumed to be the same.

DETAILED DESCRIPTION OF THE INVENTION

Figure 1:
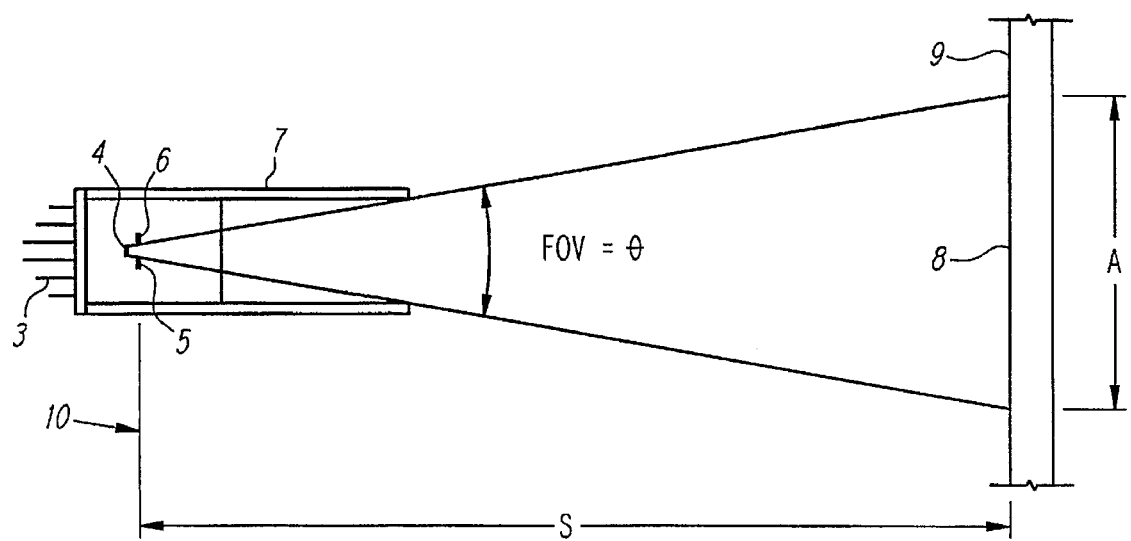
FIG. 1 shows a preferred embodiment of the present invention depicting the detector assembly, the passive infrared source (wall) and the intervening space between the passive infrared source and the detector assembly constituting the sample chamber.

A preferred embodiment of the present invention is now described with reference to FIG. 1. FIG. 1 depicts a detector assembly 3 comprising one signal detector 4 equipped with a narrow bandpass interference filter $F_1$ (not shown) whose center wavelength $L_1$ coincides with the absorption band of the gas to be measured. In addition, detector assembly 3 includes two source characterizing detectors 5 and 6 equipped respectively with narrow bandpass filters $F_2$ and $F_3$ (not shown) whose center wavelengths $L_2$ and $L_3$, do not coincide with any known gases or vapors commonly found in the atmosphere. In other words, at wavelengths $L_2$ and $L_3$, there should be no absorption bands (or at least extremely weak ones) for commonly encountered gases or vapors in the atmosphere being measured. For air, neutral wavelengths can be found at 3.91 μm, 5.00 μm, and 9.00 μm.

If carbon monoxide (CO) is the desired gas to be detected, then the center wavelength (CWL) and the full width at half maximum (FWHM) values for the interference filter associated with detector 4 are chosen to be 4.67 μm and 0.1 μm, respectively. On the other hand, if $CO_2$ is the desired gas to be detected, the CWL and FWHM for the interference bandpass filter associated with detector 4 are set at 4.26 and 0.1 μm, respectively. As one skilled in the art would recognize, this technique has application to many other gases that have an absorption band in the infrared, including $H_2O$ and Total Volatile Organic Chemicals (TVOC's).

Typically, the CWL $L_1$ of the interference filter $F_1$ associated with detector 4 will be selected so that it falls as close as possible to the middle of the absorption band being used for the gas of interest. This will ensure that the maximum amount of radiation at the spectral band being monitored is absorbed by the gas, thus increasing the sensitivity and accuracy of the detector. However, in the case of gases which are very strong absorbers like $CO_2$, it may be necessary to shift the CWL $L_1$ of the interference filter $F_1$ for detector 4 to one side of the absorption band so that not as much light is absorbed at the spectral band being monitored. Such a shift should be considered when very long pathlengths are being used or when the concentration of the gas is very high. This technique can be used to prevent the detector from becoming starved for light within the range of gas concentrations to be monitored.

The FWHM of interference filter $F_1$ associated with detector 4 is preferably selected so that it is about 0.1 μm so that the detector has a high degree of specificity.

The CWL's $L_2$ and $L_3$ of the neutral spectral bands chosen for interference filters $F_2$ and $F_3$ should be selected as close as possible to $L_1$ in spectral position. Although it is not necessary, it is also preferable for $L_1$ to fall between $L_2$ and $L_3$. For example, if CO or $CO_2$ are to be detected, $L_2$ and $L_3$ can be chosen to be 3.91 μm and 5.00 μm, respectively. Alternatively, $L_2$ and $L_3$ can be chosen to be 3.91 μm and 9.00 μm. The FWHM of $F_2$ and $F_3$ is preferably set at about 0.1 μm. The width of the spectral band passed by $F_2$ and $F_3$ should be narrow enough that it does not overlap with an absorption line of a gas that would be found in the atmosphere. By setting the CWL's of $L_2$ and $L_3$ equal to 3.91 and 5.00, respectively, and the FWHM of these detectors at 0.1 µm no significant overlap should occur. Consequently, the outputs for detectors 5 and 6 are not affected by the concentration of the gas to-be-measured or any other commonly encountered gases or vapors in the atmosphere.

Detectors 4, 5, and 6 are all preferably thermopile detectors. However, as those skilled in the art would recognize other infrared detectors may be used in the present invention, including Platinum Silicide Schottky photodiodes.

The field of view (FOV) of the detector assembly 3 is determined by the aperture collar 7 attached to the detector assembly as shown in FIG. 1. The detector assembly 3 subtends an area 8 (corresponding to area A) of the wall 9 which is used as the passive infrared source for the present invention. The effective sample path length S of the present infrared gas sensor is defined by the distance between the detector plane 10 of the detector assembly 3 and the wall 9.

The relation between the area A of the passive infrared source 8, and the solid angle subtended at it by the detector assembly 3, or OM, uniquely defines the sample path length S for the presently disclosed infrared gas sensor as follows:

Sample Path length $S=[A/OM]^{1/2}$

Since the solid angle OM is a function of the FOV subtended by the detector assembly at the wall and can be adjusted at will by design, the sample path length S for the present invention is, therefore, an extremely useful variable. In other words, the low concentration detection of a gas with an extremely weak absorption band can be accommodated by making the path length S very long (several meters) in order to attain adequate modulation for such a detection. Indeed, as one skilled in the art will recognize, the path length S should be set depending on the amount of modulation desired. For example, when a very strong absorber such as $CO_2$ is being monitored, shorter path lengths should be considered. However, if the desired application calls for detection of gas concentrations in the ppb range, then longer path lengths may be called for.

Although virtually any path length can be selected, path lengths between 5 inches and 10 feet will typically be adequate, with most path lengths being between about 5 inches and 6 feet.

The output $V_1$ of the signal detector 4 is used to determine the concentration of the gas to be measured. The output $V_1$ of detector 4 depends upon a number of factors. First and foremost, it is a function of the temperature T and the emissivity $\epsilon$ of the passive infrared source 8 as governed by the spectral radiant emittance formula depicted in Equation [1] below. Furthermore, $V_1$ also depends upon system optical throughput, or attenuation, expressed as G (see Equation [1] below) and the concentration of the to-be-measured gas found between the detector assembly 3 and the passive infrared source 8. The concentration of the gas to-be-measured determines the value of the modulation factor M as shown in Equation [1] below.

Detectors 5 and 6, which are equipped with neutral filters $F_2$ and $F_3$, are used to dynamically characterize the passive infrared source 8 and the environment in real time for the signal channel monitored by detector 4. The ratio Z of the outputs of detectors 5 and 6 uniquely determines the temperature of source 8. Furthermore, once the temperature T of the source 8 is determined, the instantaneous values for the source emissivity $\epsilon$, system optical throughput (or attenuation) G can also be quickly determined using Equation [1] below and comparing them with stored values of the respective outputs at the temperature $T_0$ and emissivity $\epsilon_0$ of a reference black body source measured while the system was initialized. The values for T, $\epsilon$ and G are continually updated in real time for the output of signal detector 4, enabling the latter to establish the concentration of the gas to be measured.

The presently disclosed simple infrared gas sensor is also capable of rejecting the influence of stray radiation by virtue of the fact that the passive infrared source 8 is generally never a good reflector. Hence the amount of stray radiation that can find its way into the FOV of the optical system is minimal. Furthermore, unless the stray radiation happens to be in the spectral band defined by the filters of the detector assembly, namely $L_2$ and $L_3$, they will be rejected. Even if they have energy within the spectral pass band of the sensor optical system, the emissivity is likely to be rather smooth and constant. In such a case, the neutral detectors will simply treat such stray radiation as an increase in the passive infrared source temperature 8 with the correct information related to the signal detector for proper processing.

The manner in which the concentration of the gas to-be-measured is determined from the outputs $V_1$, $V_2$, and $V_3$ of detectors 4, 5, and 6, respectively is now described in connection with FIGS. 2 and 3.

Figure 2:
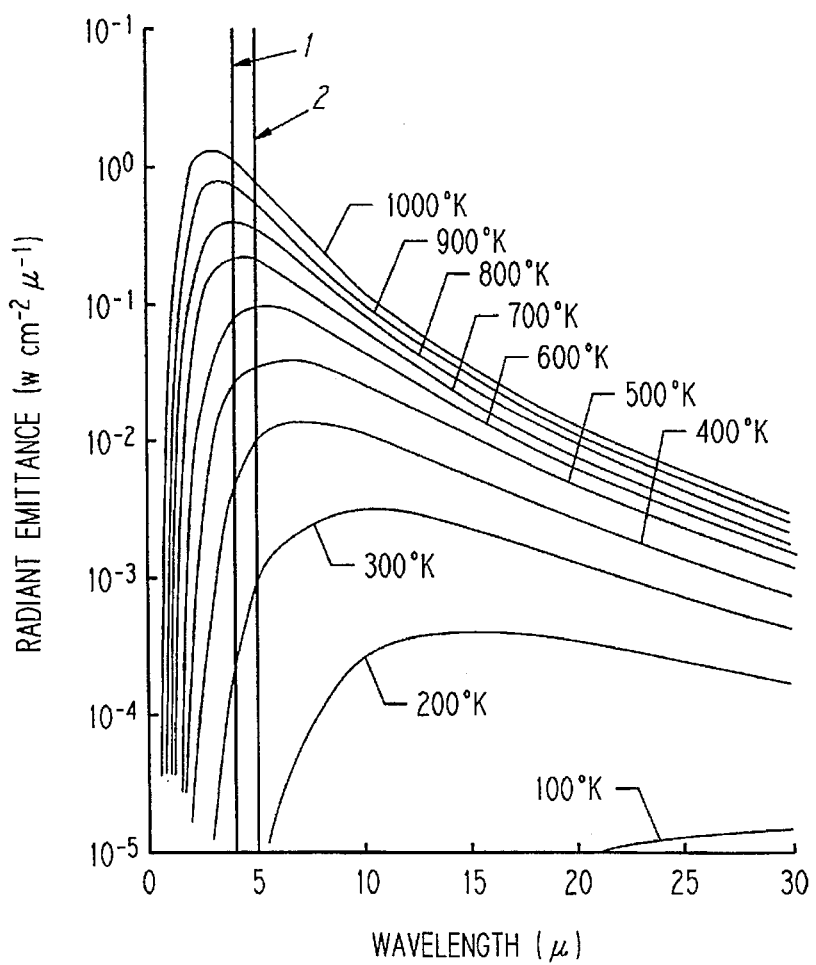
FIG. 2 is a graph showing the spectral radiant emittance of a black body at temperatures 100°–1,000° K.

FIG. 2 shows the spectral radiant emittance of a black body source at temperatures ranging from 100 K to 1,000 K. Several characteristics of the radiation from a black body source can be derived from these curves. First, the total radiant emittance which is proportional to the area under the curves, increases rapidly with temperature. The area under the curves being defined by the Stefan-Boltzmann equation and is thus proportional to the Stefan-Boltzmann constant times the absolute temperature to the fourth power. Second, the wavelength of maximum spectral radiant emittance shifts towards shorter wavelength as the temperature increases. This is referred to as Wien's displacement law, which is discussed more fully below. Third, the individual black body curves never cross one another; hence the higher the temperature, the higher the spectral radiant emittance at all wavelengths.

In conventional NDIR measurement systems using a black body, the infrared source is normally maintained at a constant and relatively high temperature (750–1,000 K), and thus its spectral radiant emittance is typically represented by one of the curves above 700 K in FIG. 2 dependent upon its absolute temperature. In contrast, the present invention relies on infrared radiation from passive infrared sources. As a result, the black body curves around 300 K will typically reflect the radiant emittance of the typical sources used with the present invention. Such is the case with the wall 9 in FIG. 1.

The two narrow spectral bands 1 and 2 illustrated in FIG. 2 are centered at 3.91 µm and at 5.00 µm, which, as discussed above are desirable wavelengths for neutral detectors 5 and 6 when monitoring CO or $CO_2$. Because the bands illustrated in FIG. 2 correspond to the neutral spectral bands allowed to pass filters $F_2$ and $F_3$, they would preferably have a FWHM of 0.1 µm.

As seen from FIG. 2, the ratio (Z) of the spectral radiant emittances at these two wavelengths uniquely determines the black body temperature. The only assumption made in this assertion is that the emissivity of the "passive" infrared source is approximately the same within the spectral band bounded by 3.91 µm and 5.00 µm. For almost all indoor walls which are either painted, wall-papered or wood-paneled, this is a good assumption.

Before determining the concentration of the gas being monitored, the passive source 8 must be characterized. The manner whereby the detectors 5 and 6 dynamically characterize the temperature and the emissivity of the passive infrared source 8 for the signal channel 4 is described as follows. For purposes of this discussion, detectors 4, 5, and 6 will be referenced as detectors $D_1$, $D_2$, and $D_3$.

Assuming that all three detector outputs $V_1$, $V_2$ and $V_3$ are initially referenced (i.e., initialized) to have values $V_{10}$, $V_{20}$ and $V_{30}$, respectively, at a known "passive" infrared source having temperature $T_0$, $\epsilon_0$ and area $A_0 = OM \times S^2$, where OM is the solid angle corresponding to the FOV of the detector assembly 3 subtended by the passive source at the detector assembly, and S is the defined sample path length, one can write:

$$V_{i0} = R(T_0, \epsilon_0, L_i) \times A \times W_i \times r_i \times (a_i/(2\pi S^2)) \times G \times M \text{ volts} \quad [1]$$

where i=1, 2 or 3;

$R(T_0, \epsilon_0, L_i) = \epsilon_0$ of the known passive infrared source multiplied by the Black body Spectral Radiant Emittance (Watt cm$^{-2}$ µ$^{-1}$);

A=Area of passive infrared source;

$W_i$=FWHM of $F_i$;

$r_i$=Responsivity of detector $D_i$ (Volts/Watt);

$a_i$=Area of detector $D_i$;

S=Sample path length;

G=System Optical Throughput (100%=unity);
and

M=Modulation by the gas to be measured.

When the detector assembly 3 faces a real time passive infrared source 8 of the area A (A is the same as the reference condition because OM and S are fixed by design in the embodiment illustrated in FIG. 1), temperature T and emissivity $\epsilon$, the outputs of $D_1$ are given by Equation [1] above as follows:

$$V_i = R(T, \epsilon, L_i) \times A \times W_i \times r_i \times (a_i/(2\pi S^2)) \times G \times M$$

where i=1

For the neutral channels $D_2$ (i=2) and $D_3$ (i=3), if we assume that $W_2 = W_3$; $r_1 = r_2$ (similar detectors); $a_2 = a_3$ (same detector areas); $G_2 = G_3$ (both detectors share the common optical system) and M=1.0 (neutral spectral bands for both $D_2$ and $D_3$), then the outputs of the detectors $D_2$ and $D_3$, namely $V_2$ and $V_3$, are the functions only of their respective spectral position $L_2$ and $L_3$, the temperature T and the emissivity $\epsilon$ of the passive infrared source 8. If we further assume that the emissivity $\epsilon$ of the passive infrared source 8 is the same for the narrow spectral region bounded by $L_2$ and $L_3$ (about one micron), then the ratio of the outputs $Z = V_2/V_3$ is only a function of temperature T of the passive infrared source 8, and the spectral positions $L_2$ and $L_3$.

As a matter of fact, the Planckian black body radiation physics together with the Wien's displacement law stipulate that the ratio of the spectral radiant emittances at two spectral positions, when appropriately spaced, uniquely determines the temperature of a particular black body source in certain parts of the Planckian black body domain. The present invention takes advantage of this fact and recognizes that in the spectral regions between 3–15 microns and black body temperatures between 250–350 K, such a ratio can indeed uniquely determine the temperature of the black body. Furthermore, once the temperature T from the reference temperature $T_0$ is determined, the present value $V_2$ or $V_3$ of the respective neutral detector outputs can be used to deduce by calculations the changes (if any) for the other parameters, grouped together as a product, in Equation [1] above, namely the emissivity $\epsilon$ of the passive infrared source 8 from $\epsilon_0$, the change in the system optical throughput G and the change in the detector responsivity due to aging of the detector itself.

Thus by adding two detectors with neutral spectral bands to the detector assembly of the present invention, the ratio of the outputs Z of these two detectors can be used to characterize in real time the temperature of the passive infrared source 8. However, it is important to point out that the FWHM (i.e. $W_i$) of the neutral detectors should be the same so that this factor cancels out when the ratio Z is calculated. It is also important to point out that since the changes in the other parameters in Equation [1] above, namely $\epsilon$, G and r are substantially the same for the two neutral detector channels, the value of the ratio Z, which is the only parameter needed to determine uniquely the temperature of passive infrared source 8, can always be obtained firsthand. After this vital information is attained, the individual preset values of the signal and neutral detector outputs ($V_{10}$, $V_{20}$, $V_{30}$, $T_0$, and $\epsilon_0$) can be used to further assess, via calculations, any changes in the other parameters in Equation [1]. Since the parameters needed to determine the concentration of the gas to-be-measured from the signal channel detector output in Equation [1] are T, $\epsilon$, G, r and M, and since the first four parameters are dynamically characterized by the two neutral detector channels for the signal detector channel, the present invention, as illustrated in the present embodiment, is capable of accurately measuring the concentration of gas without the need for an active infrared source and the accompanying gas sample chamber.

FIG. 3 illustrates how the ratio of the spectral radiant emittances at 3.91 µm and 5.00 µm varies as a function of the passive infrared source temperature from 5° C. (278 K) to 45° C. (318 K). In the vicinity of the 300 K black body curves, the curves themselves are smooth and there is a very respectable difference in the value of the ratio as a function of the black body temperatures.

As would be readily apparent to those skilled in the art from the foregoing, the infrared gas detector can be used to monitor the concentration of a plurality of gases simply by adding additional detectors $D_i$ to the detector assembly 3 and appropriately selecting the CWL of interference filter $F_i$ to correspond to the characteristic absorption band of the gas desired to be monitored.

Figure 4:
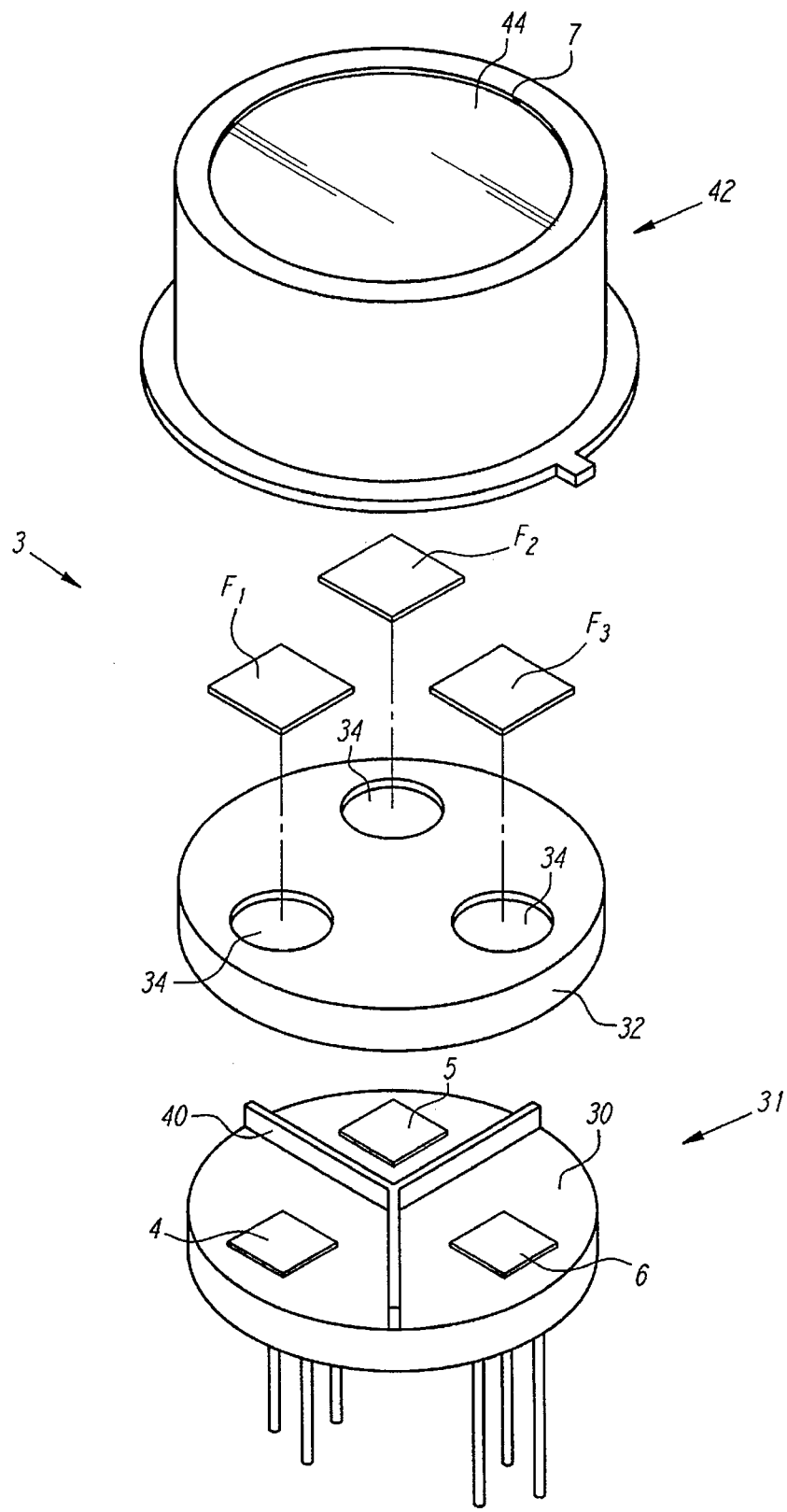
FIG. 4 is an exploded view of a detector assembly according to an embodiment of the present invention.
Figure 5:
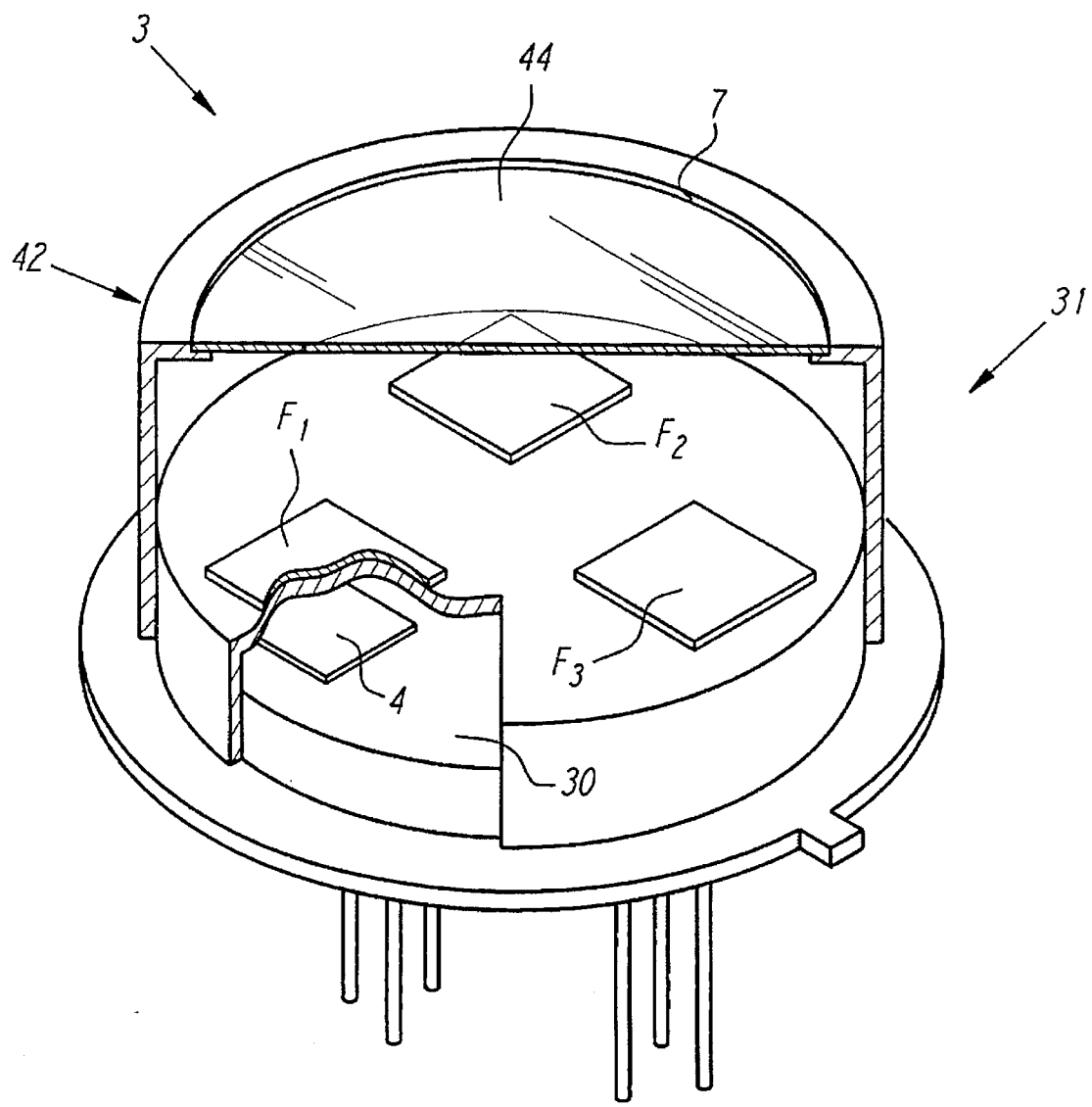
FIG. 5 is an oblique view showing a partial cutaway of the detector assembly illustrated in FIG. 4.

The construction of a particularly preferred detector assembly 3 is illustrated in FIGS. 4 and 5. As illustrated, the detector assembly is produced on a TO-5 can 31. The infrared detectors 4, 5 and 6 are mounted on a housing base 30 of the TO-5 can 31. Infrared detectors 4, 5 and 6 are in close proximity to one another so that the field of view of each detector overlaps substantially with one another.

While a variety of infrared detectors can be used in the present invention, detectors 4, 5 and 6 are preferably thermopiles due to the fact that thermopiles do not require any power, have a linear output, and have a very good signal to noise ratio. Although not required, it is also preferable to tie the reference junctions of each of the three detectors to the same thermal heat sink.

Filter mount 32 is disposed on top of housing base 30 so that the only radiation which can enter the space between the filter mount 32 and housing base 30 is the radiation that enters through the three apertures 34 located in filter mount 32. Apertures 34 are located in filter mount 32 so that each aperture is in axial alignment with one of the detectors.

Interference bandpass filters $F_1$, $F_2$ and $F_3$ cover apertures 34 so that they are interposed between the respective detector and the passive infrared light source. Furthermore, by covering the three apertures 34 located in filter mount 32 with interference filters $F_1$, $F_2$ and $F_3$, it is ensured that the only radiation that can enter the space between the filter mount 32 and the housing base 30 is that of the desired spectral bands. Divider 40 is used to prevent light of one spectral band from coming in contact with an infrared detector intended to measure light from a different spectral band.

The CWL and FWHM of bandpass filters $F_1$, $F_2$ and $F_3$ are set as described in connection with FIG. 1.

The lid 42 to TO-5 can 31 acts as aperture collar 7 and thus defines the FOV for the detector assembly 3. The top of lid 42 comprises a light transmissive window 44. In selecting the material for window 44, it is preferable to select a material that is as transmissive as possible to the spectral bands being monitored by the detector assembly 3. Preferably, window 44 is equally transmissive for each of the spectral bands being monitored. Window materials which have relatively uniform transmission qualities over the range of 1 μm to 10 μm include silicon, $CaF_2$, and $BaF_2$. $CaF_2$ and $BaF_2$ are particularly preferred materials because of their high transmissivity in this range.

To save costs, window 44 may be eliminated altogether. However, by including window 44, the detector assembly 3 illustrated in FIGS. 4 and 5 can be hermetically sealed. Further, as dust and grease builds up on the detector assembly 3, the output signal corresponding to the spectral bands will begin to drop. If the attenuation of the signal becomes too large, the infrared gas detector will not function properly. However, by including window 44 in detector assembly 3, the original signal strength can be easily restored by cleaning window 44. This is not possible if window 44 is omitted.

If a larger platform is desired so that additional detectors and bandpass filters can be added to enhance the capabilities of the infrared gas detector of the present embodiment, a TO-8 package can be selected. For instance, such a platform might be used if the ability to monitor a plurality of gases is desired.

Figure 6:
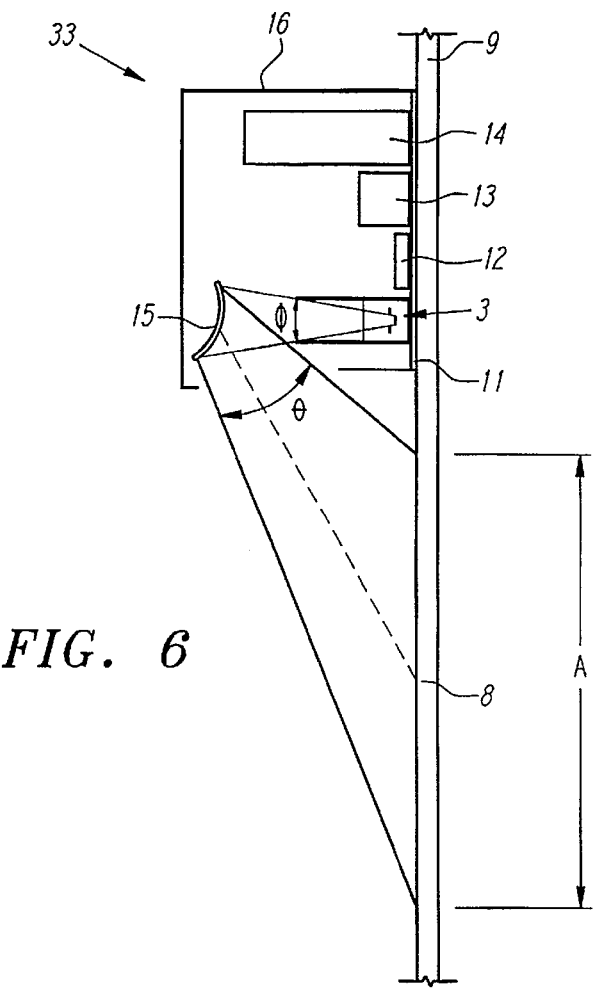
FIG. 6 shows an alternate preferred embodiment for the current invention depicting the actual use of a portion of a wall as the "passive" infrared source and the use of a convex spherical reflector to increase the original field of view (FOV) of the detector assembly.

FIG. 6 shows another preferred embodiment of the present invention as the implementation of an actual PIA gas sensor 33 according to the present invention for the detection of a gas. The detector assembly 3 is mounted directly on the printed circuit board (PCB) 11 which also is a mount for the signal processing electronics 12, siren 13 for sounding an alarm and a battery power source 14. Battery power source 14 is preferably a lithium battery, which should provide sufficient power to operate the system from 1 to 2 years.

Spherical reflector 15, which is affixed rigidly to the detector assembly 3, is used to increase the FOV of the detector assembly 3. The sample path length for the gas sensor in this case is again defined by the distance between the detector assembly 3 and the passive infrared source 8, which is defined as a portion of the wall 9. The PCB 11 carrying all the components described earlier is housed in an enclosure 16 for protection from handling and external environments when being used to implement the PIA technique of the present invention.

As one skilled in the art would recognize, the FOV of detector assembly 3 can similarly be enhanced by using a refractive optics system instead of reflective optics system. Refractive optics are preferred, however, because of their cost.

Figure 7:
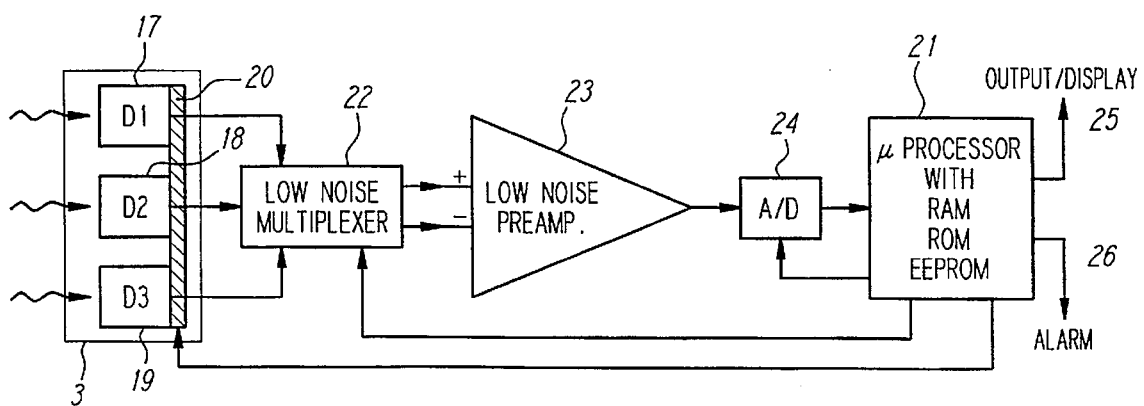
FIG. 7 shows a schematic drawing for the signal processing circuits for a preferred embodiment of the present invention.

FIG. 7 shows the schematic drawing for the signal processing circuits according to a preferred embodiment for the present invention. The signal processing circuits illustrated in FIG. 7 can be used in conjunction with the detector assembly embodiments illustrated in FIGS. 1, and 4–6.

According to the present embodiment, infrared radiation emanating from the passive source (not shown) is collected within the FOV of the detector assembly 3 onto detectors 17, 18 and 19 representing respectively the signal detector $D_1$, and the neutral detectors $D_2$ and $D_3$. The detectors 17, 18 and 19 are thermopile detectors and their reference junctions are tied thermally to the same heat sink 20. One of the major advantages of the thermopile detectors is their linear output (scalable linearly with temperature from 0° to 70° C.). Thus, the outputs of the detectors 17, 18 and 19 can be corrected for environmental temperature changes by sensing the same at the common reference junction heat sink 20 using microprocessor 21.

In order to minimize DC drifts, each of the three detectors outputs are subsequently switched with the same duty factor by a low noise multiplexer 22 controlled by the microprocessor 21 to the differential input of the same low noise preamplifier 23. The amplified signals are then converted by an A/D converter 24 before being fed into the microprocessor 21 for signal processing. After the gas to be measured is detected, the concentration of the gas can be monitored based on a predetermined function programmed into microprocessor 21. The concentration can be outputted or displayed using cable 25 or in some cases an alarm signal can also be generated by the microprocessor 21 using cable 26.

Microprocessor 21 is of the low power type and contains enough RAM, ROM and EEprom for appropriately processing the signals originated by the detector assembly 3.

The versatility of the infrared gas detectors of the present invention could be further enhanced by adding a distance measuring device to the gas detector. This would permit the user to quickly and easily modify the sample length S depending on the application. The distance measuring device could be of the contact or non-contact type. For example, it could comprise a laser diode with a sensor as is well known in the art. The output of the distance measuring device would be communicated to the signal processor so that the appropriate sample path length S can be inserted into equation [1] when calculating the concentration of the gas. As discussed above, the change in the path length is not required for calculating the ratio of the outputs from the two neutral channels, because this factor would cancel out since it would be the same for both detectors.

Alternatively, the gas detector can include a switch so that the user can enter preset pathlengths. For example, the switch might include path length settings increasing by one foot increments so that the user can measure and enter the appropriate path length for the set up in which the gas detector of the present invention is being used. The selection of a particular path length is communicated to the microprocessor 21 so that it knows the appropriate path length to use in calculating the concentration of the gas in the sample volume.

For slightly more flexibility, a data entry pad can be used so that the user can enter any desired path length and the microprocessor 21 will compensate accordingly during its calculations.

Figure 8:
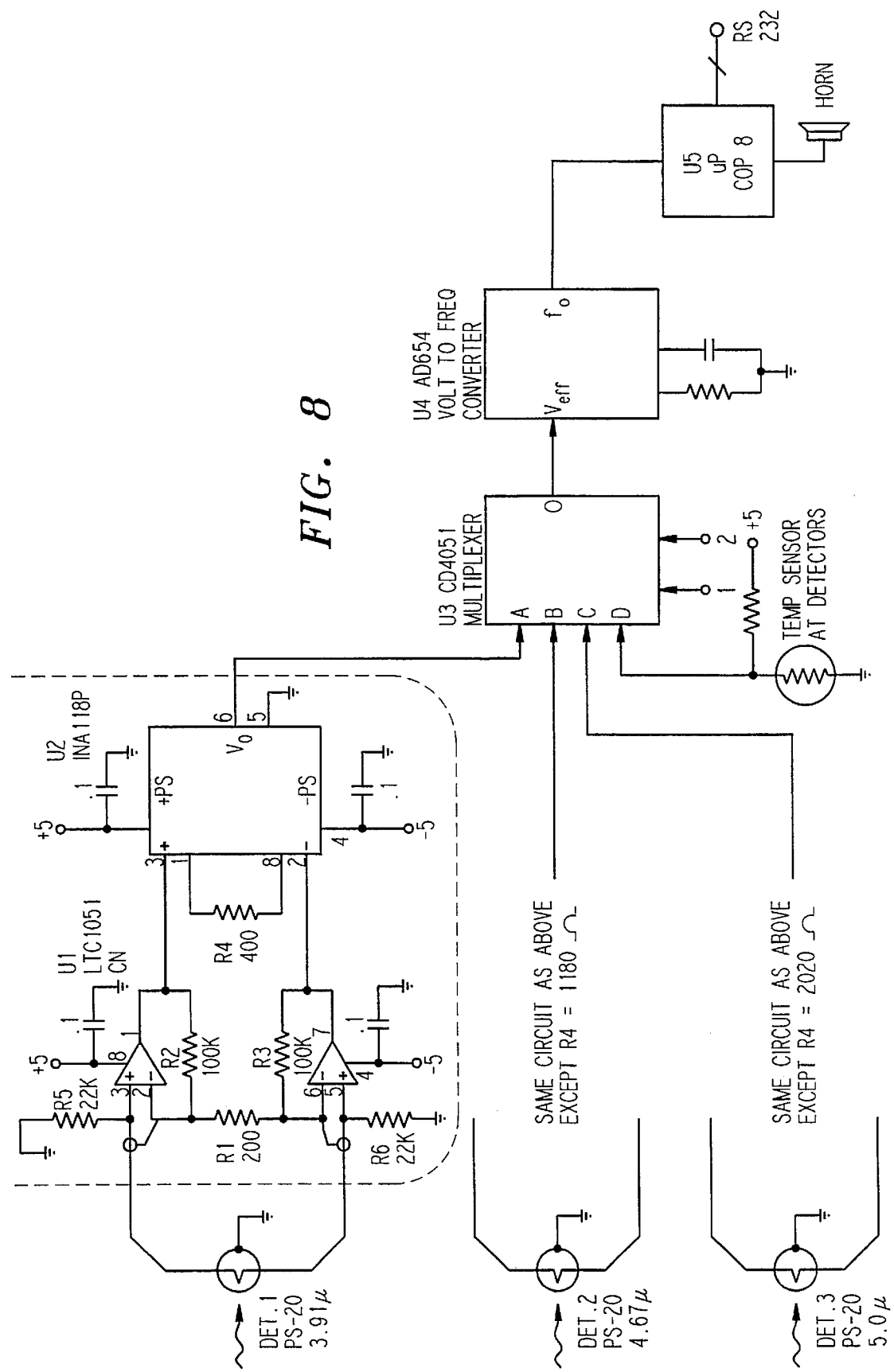
FIG. 8 shows the circuit schematic for the signal processor according to another embodiment of the present invention.

FIG. 8 is a circuit schematic for a signal processor according to another embodiment of the present invention. The structure of the circuit is determined by the low level of the expected signals, in the order of 5 to 85 μVolt. There are three identical preamplifier circuits which differ only in the value of a gain setting resister, R4. The amplifiers are constructed in the form of instrumentation, amplifiers which have a very high common mode signal rejection, because for operation in the home near 60 Hz power wiring large signals may be induced magnetically. Magnetic shielding of the detectors and circuits should reduce this. The detectors and circuit components should also be protected from rapid temperature changes which can produce thermocouple signals in the components. The thermal and mechanical design are very important to allow the full capabilities of the electronic circuit.

U1 forms the input part of the instrumentation amplifier. It was selected for its very low input offset voltage, about 0.5 μV, and very low change of that voltage with temperature. For high common mode rejection the two feedback resistors R2 and R3 should be matched to better than 0.1%, and should have temperature coefficients of 10 ppm/deg C or better. The gain of this circuit is determined by the ratio of R2 and R3 to R1, about 500. The noise level for dc to 10 Hz is about 2 μV pp. This is higher than is desirable, but it can be filtered later. The low input offset and drift with temperature are more important to obtain proper processing of the sampled outputs.

The input noise level of the output part of the circuit is much lower, about 0.28 μV, but the offset is much higher, about 50 μV, and with a larger temperature coefficient. U2 is actually another instrumentation amplifier. It is used to provide a stable high gain of about 400. It is used because it is less expensive than another amplifier and four accurate gain setting resistors. The expected output is from one to two volts or more, depending on the input radiation to the detector. The gains of the preamps for the other two detectors are lower since more radiation is expected at the longer wavelengths of those detectors.

The rest of the signal processing can be handled in many different ways, one implementation is shown as an example. The three signal channels and one temperature sensor near the detectors are selected by a multiplexer, and their value converter to a frequency by a voltage to frequency converted. The frequency output can be processed easily by a microprocessor (μP), to determine the temperature of the scene viewed, the temperature of the detectors, and then the absorption due to CO gas, or other gas to be measured, from the expected signals at those temperatures.

While the present invention has been made clear in the illustrative embodiments, it will be immediately obvious to those skilled in the art that many modifications of structure, arrangement, proportions, the elements, materials, and components used in the practice of the invention, and otherwise, which are particularly adapted to specific environments and operative requirements, can be made without departing from the principles disclosed. Thus, it is to be clearly understood that this description is made only by way of example and not as a limitation to the scope of the invention as claimed below.

I claim:
1. A passive source infrared gas detector, comprising:
   a. an infrared detector assembly comprising
      i. a port for receiving radiation therethrough from the passive infrared source,
      ii. a first sensor, a second sensor, and a third sensor disposed to receive radiation through the port for producing a first output, a second output, and a third output indicative of the radiation incident on the first sensor, second sensor, and third sensor, respectively,
      iii. a first narrow band pass filter interposed between the port and the first sensor, the first narrow band bass filter producing an output therefrom indicative of the radiation incident on the first band pass filter at a first non-neutral spectral band which is absorbable by a preselected gas to be detected,
      iv. a second narrow band pass filter interposed between the port and the second sensor, the second narrow band pass filter producing an output therefrom indicative of the radiation incident on the second band pass filter at a first neutral spectral band, and
      v. a third narrow band pass filter interposed between the port and the third sensor, the third narrow band pass filter producing an output therefrom indicative of the radiation incident on the third band pass filter at a second neutral spectral band,
   b. temperature measuring means for producing an output corresponding to the ambient temperature of the first, second, and third sensors;
   c. signal processing means adapted to receive the outputs from the first sensor, second sensor, third sensor, and temperature measuring means and for sampling and at least temporarily storing the outputs of the first sensor, second sensor, third sensor, and temperature measuring means at preset intervals, the signal processing means including means for
      i. correcting the stored outputs of the first sensor, second sensor, and third sensor to compensate for the ambient temperature of the first sensor, second sensor, and third sensor, respectively, at the time of sampling,
      ii. calculating the temperature of the passive infrared source at the time of sampling based on the ratio of the corrected values of the outputs from the second and third sensors,
      iii. calculating a predicted output for at least one of the second or third sensors based on the calculated temperature of the passive infrared source for the sampling period,
      iv. calculating an attenuation factor by comparing the predicted output of at least one of the second or third sensors with the corrected output from the corresponding sensor for the sampling period,
      v. correcting the stored output of the first sensor by the attenuation factor,
      vi. determining the concentration of the gas for the sampling period from the corrected output from the first sensor, and
      vii. monitoring the concentration of gas based on a predetermined function and providing an output signal based on the monitoring.

2. A passive infrared gas detector according to claim 1, wherein the first sensor, second sensor, and third sensor each comprise a thermopile detector.

3. A passive infrared gas detector according to claim 1, wherein the first sensor, second sensor, and third sensor each comprise a thermopile and each share a common reference junction.

4. A passive infrared gas detector according to claim 1, wherein the field of view for the first, second, and third sensors is substantially the same.

5. A passive infrared gas detector according to claim 4, further comprising an optical system which expands the field of view of the detector assembly.

6. A passive infrared gas detector according to claim 1, wherein the gas being monitored is at least one selected from the group consisting of CO, $CO_2$, $H_2O$, and TVOC.

7. A passive infrared gas detector according to claim 1, wherein the first, second, and third narrow band pass filters are about 0.1 μm wide at FWHM.

8. A passive infrared gas detector according to claim 7, wherein the second and third narrow band pass filters have a center wavelength selected from the group consisting of about 3.91 μm, about 5.0 μm, and about 9.0 μm.

9. A passive infrared gas detector according to claim 8, wherein the first narrow band pass filter has a center wavelength of about 4.67 μm.

10. A passive infrared gas detector according to claim 1, further comprising a battery power source.

11. A passive infrared gas detector according to claim 1, wherein the port comprises a window in a TO-5 can.

12. A passive infrared gas detector according to claim 1, wherein the output of the signal processing means is communicated to an alarm.

13. A passive infrared gas detector according to claim 1, wherein the infrared detector assembly is housed in a TO-5 can.

14. A passive source infrared gas detector, comprising:
   a. an infrared detector assembly for producing a first output, a second output, and a third output, the first output being indicative of the radiation received by the detector assembly at a first non-neutral spectral band which is absorbable by a preselected gas to be detected, the second output being indicative of the radiation received by the detector assembly at a first neutral spectral band from the passive infrared source, and the third output being indicative of the radiation received by the detector assembly at a second neutral spectral band from the passive infrared source;
   b. temperature measuring means for producing an output indicative of the ambient temperature of the detector assembly;
   c. signal processing means adapted to receive the first, second, and third outputs and the output from the temperature measuring means and for sampling and storing, at least temporarily, the first, second, and third outputs and the output from the temperature measuring means at preset intervals, the signal processing means including means for
      i. correcting the stored first, second, and third outputs to compensate for the ambient temperature of the detector assembly,
      ii. calculating the temperature of the passive infrared source based on the ratio of the corrected values of the stored second and third outputs,
      iii. calculating a predicted second or third output for the sampling period based on the calculated temperature of the passive infrared source,
      iv. calculating an attenuation factor for the sampling period by comparing the predicted second or third output with the actual stored second or third output, respectively,
      v. correcting the stored first output by the attenuation factor calculated for the sampling period,
      vi. determining the concentration of the gas for the sampling period using the corrected first output, and
      vii. monitoring the concentration of gas based on a predetermined function and providing an output signal based on the monitoring.

15. A passive infrared gas detector according to claim 14, wherein the gas to be detected is at least one selected from the group consisting of CO, $CO_2$, $H_2O$, and TVOC.

16. A passive infrared gas detector according to claim 14, wherein the first non-neutral spectral band, the first neutral spectral band, and the second neutral spectral band are about 0.1 µm wide at FWHM.

17. A passive infrared gas detector according to claim 16, wherein the first neutral spectral band and the second neutral spectral band have a center wavelength selected from the group consisting of about 3.91 µm, about 5.0 µm, and about 9.0 µm.

18. A passive infrared gas detector according to claim 17, wherein the first non-neutral spectral band has a center wavelength of about 4.67 µm.

19. A passive infrared gas detector according to claim 17, wherein the first non-neutral spectral band has a center wavelength of about 4.26 µm.

20. A passive infrared gas detector according to claim 14, further comprising a battery power source.

* * * * *